US010206896B2

(12) United States Patent
Bitar et al.

(10) Patent No.: US 10,206,896 B2
(45) Date of Patent: Feb. 19, 2019

(54) METHOD OF TREATING DELAYED HEALING OF A WOUND ASSOCIATED WITH DIABETES

(71) Applicant: KUWAIT UNIVERSITY, Safat (KW)

(72) Inventors: Milad S. Bitar, Salmiya (KW); Fahd Al-Mulla, Al-Yarmouk (KW)

(73) Assignee: Kuwait University, Safat (KW)

( * ) Notice: Subject to any disclaimer, the term of this patent is extended or adjusted under 35 U.S.C. 154(b) by 0 days.

(21) Appl. No.: 16/020,517

(22) Filed: Jun. 27, 2018

(65) Prior Publication Data

US 2018/0311193 A1 Nov. 1, 2018

Related U.S. Application Data

(62) Division of application No. 14/301,301, filed on Jun. 10, 2014, now abandoned.

(51) Int. Cl.
| | |
|---|---|
| *C07H 21/02* | (2006.01) |
| *C07H 21/04* | (2006.01) |
| *A61K 31/70* | (2006.01) |
| *A61K 31/19* | (2006.01) |
| *C12N 15/113* | (2010.01) |
| *A61K 31/56* | (2006.01) |
| *C12N 5/00* | (2006.01) |

(52) U.S. Cl.
CPC .............. *A61K 31/19* (2013.01); *A61K 31/56* (2013.01); *C12N 15/113* (2013.01); *C12N 2310/11* (2013.01); *C12N 2310/14* (2013.01); *C12N 2310/3233* (2013.01)

(58) Field of Classification Search
None
See application file for complete search history.

(56) References Cited

U.S. PATENT DOCUMENTS

| | | | | |
|---|---|---|---|---|
| 8,409,603 | B2 * | 4/2013 | Gourdie | A61K 35/28 424/423 |
| 8,449,879 | B2 * | 5/2013 | Laurent-Applegate | A61K 38/014 424/426 |
| 2009/0226427 | A1 | 9/2009 | Balligand et al. | |
| 2009/0318454 | A1 | 12/2009 | Weiner et al. | |
| 2011/0038799 | A1 | 2/2011 | Park et al. | |
| 2011/0038920 | A1 * | 2/2011 | Mori | C12N 15/1136 424/445 |
| 2012/0213737 | A1 | 8/2012 | Zhu et al. | |
| 2013/0040953 | A1 | 2/2013 | Paller | |
| 2013/0171210 | A1 * | 7/2013 | Baker | A61K 9/0014 424/400 |
| 2013/0243734 | A1 * | 9/2013 | Green | A61K 31/711 424/93.7 |
| 2015/0352064 | A1 * | 12/2015 | Bitar | A61K 31/19 514/44 A |

FOREIGN PATENT DOCUMENTS

JP 10-87698 4/1998

OTHER PUBLICATIONS

Zhu, Hua et al., "Polymerase Transcriptase Release Factor (PTRF) Anchors MG53 Protein to Cell Injury Site for Initiation of Membrane Repair", Journal of Biological Chemistry, 286(15), 12820-12824, Apr. 15, 2011.
D. Volonte et al., "Expression of caveolin-1 induces premature cellular senescence in primary cultures of murine fibroblasts", Mol. Biol. Cell. (2002), 13(7), pp. 2502-2517.
D. Volonre et al., "Polymerase 1 and transcript release factor (PTRF)/cavin-1 is a novel regulator of stress-induced premature senescence", J. Biol. Chem. (2011) 286(33), pp. 28657-28661.
M.S. Bitar et al. "Caveolin-1/PTRF upregulation constitutes a mechanism for mediating p53-induced cellular senescence: implications for evidence-based therapy of delayed wound healing in diabetes", Am J Physiol Endocrinol Metab (Oct. 2013; published elec. Aug. 13, 2013), 305(8) E951-63.
Al-Mulla F., Leibovich S.J., Francis I.M., Bitar, M.S., "Impaired TGF-beta signaling and a defect in resolution of inflammation contribute to delayed wound Healing in a Female Rat Model of Type 2 Diabetes," Mol. Biosyst. 7(11): 3006-3020 (2011).
Bitar, M.S., Al-Mulla, F., A Defect in Nrf2 Signaling Constitutes a Mechanism for Cellular Stress Hypersensitivity in a Genetic Rat Model of Type 2 Diabetes, Am. J. Physiol. Endocrinol. Metab., 301(6):E111-1129 (2011).
Bitar, M.S., Al-Mulla, F., "ROS Constitute a Convergence Nexus in the Development of IGF1 Resistance and Impaired Wound Healing in a Rat Model of Type 2 Diabetes" (2012).
Dasari A, Bartholomew JN, Volonte D, Galbiati F. 2006. Oxidative stress induces premature senescence by stimulating caveolin-1 gene transcription through p38 mitogen-activated protein kinase/Sp1-mediated activation of two GC-rich promoter elements. Cancer Res 66(22):10805-10814.
Clark RA. 2008. Oxidative stress and "senescent" fibroblasts in non-healing wounds as potential therapeutic targets. J Invest Dermatol 128(10):2361-2364.

(Continued)

*Primary Examiner* — Sean McGarry
(74) *Attorney, Agent, or Firm* — Richard C. Litman

(57) ABSTRACT

The method of treating delayed healing of a wound associated with diabetes includes administering to the wound a composition comprising an anti-senescence compound and a pharmaceutically acceptable carrier. The anti-senescence compound may be 18α-Glycyrrhetinic acid, a Caveolin-1 (Cav-1) inhibitory compound, or a Polymerase I Transcript Release Factor (PTRF-1) inhibitory compound. The anti-senescence compound may be effective in preventing and/or reversing premature cellular senescence. The anti-senescence compound may be effective in promoting healing of a wound, e.g., delayed or incompletely healed wound. The anti-senescence compound may be effective in promoting healing of a delayed healing wound or chronic wound of a diabetic patient, such as a diabetic ulcer or venous ulcer.

8 Claims, 7 Drawing Sheets

(56) References Cited

OTHER PUBLICATIONS

Bai L, Deng X, Li J, Wang M, Li Q, An W, A D, Cong YS. 2011. Regulation of cellular senescence by the essential caveolar component PTRF/Cavin-1. Cell Res 21(7):1088-1101.
Bartholomew JN, Volonte D, Galbiati F. 2009. Caveolin-1 regulates the antagonistic pleiotropic properties of cellular senescence through a novel Mdm2/p53-mediated pathway. Cancer Res 69(7):2878-2886.
Any identified foreign patents and/or publications have been properly submitted in parent U.S. Appl. No. 14/301,301, filed Jun. 10, 2014, the priority of which is claimed.

* cited by examiner

METHOD OF TREATING DELAYED HEALING OF A WOUND ASSOCIATED WITH DIABETES

CROSS REFERENCE TO RELATED APPLICATIONS

This application is a division of Ser. No. 14/301,301, filed Jun. 10, 2014.

BACKGROUND OF THE INVENTION

1. Field of the Invention

The present invention relates to the treatment of wounds, and particularly to a method of treating delayed healing of a wound associated with diabetes, and particularly premature cellular senescence induced by diabetes.

2. Description of the Related Art

Diabetic ulcers, such as diabetic foot ulcers, are a major complication of diabetes mellitus. Diabetic foot ulcers, in particular, occur in 15% of all patients with diabetes and precede 84% of all lower leg amputations. Major increases in mortality among diabetic patients, observed over the past 20 years, is considered to be due to the development of macro- and micro-vascular complications, including failure of the wound healing process.

Wound healing is an innate mechanism of action that works reliably most of the time. A key feature of wound healing is stepwise repair of lost extracellular matrix (ECM), which forms the largest component of the dermal skin layer. Controlled and accurate rebuilding is essential to avoid the under- or over-healing that may lead to various abnormalities. However, in some cases, certain disorders, such as diabetes mellitus, or physiological insult disturbs the wound healing process. Many histopathological studies show a prolonged inflammatory phase in diabetic wounds, which causes a delay in the formation of mature granulation tissue and a parallel reduction in wound tensile strength.

During the course of wound healing, dermal fibroblasts play dual functions as a synthetic cell, which deposits the extracellular matrix, and a signaling cell, which synthesizes and secretes the growth factors essential for tissue repair. Normal fibroblasts can typically divide 50-70 times in tissue culture before they become senescent. This phenotype is characterized by the enlargement and spreading of the cells, an accumulation of lipofuscin, the expression of senescence-associated β-galactosidase (SA-β-gal), cell cycle arrest in G1, and an increase in polynucleation. These cells can be exploited by the tumor microenvironment to limit the progression of certain cancer types, but they may also have a detrimental influence on injured tissue regeneration. Cellular senescence can also be induced by stressors (stress-induced premature senescence, SIPS), such as reactive oxygen species (ROS), of which hydrogen peroxide (HP) is the most common. Other known stressors include hyperoxia, ultraviolet light, γ-irradiation, and oncogenic stimulation. Most of these SIPS-related paradigms are associated with the activation of p53-, p21- and/or p16-retinoblastoma protein-dependent pathways.

Cellular senescence constitutes a mechanism that inhibits mammalian cell growth in response to damage or stress. This process plays a crucial role in age-related diseases and tumorigenesis, and appears to be associated with accumulated DNA damage, a limited number of cell divisions, and a reduced ability to remove free radicals.

Cellular senescence represents a major contributing factor in the induction of non-healing chronic wounds. Studies have shown that cell replicative ability was diminished by approximately 50% in pressure ulcer fibroblasts compared to adjacent normal fibroblasts. Similarly, an increase in fibroblast senescence appears to predominate in the venous ulcers and skin tissue of diabetic mice. Consistent with these findings, it was reported that a number of senescence-like features (e.g., the increased expression of SA-β-gal; decreased production of cyclin D1, phosphorylated RB, and growth factors; and increased level of p21) can be recapitulated by exposing normal fibroblasts in culture to wound fluids derived from chronic non-healing wounds. It is noteworthy that the most common features of these chronic wound microenvironments include markedly increased ROS levels (an active species that attacks DNA, causing the accumulation of lipofuscin [a molecule that cannot be degraded by cells] and DNA damage-induced cell cycle arrest), the decreased expression and secretion of growth factors (EGF, KGF, PDGF and IGF-1), decreased keratinocyte migration, increased tissue proteases, and microbial contamination. The recognition of the impact of senescence on wound healing is only just emerging.

Non-healing chronic diabetic ulcers are typically treated with extracellular matrix replacement therapy. At present, diabetic foot care largely includes advanced moist wound therapy, bio-engineered tissue or skin substitute, growth factors, and negative pressure wound therapy. None of these therapies, however, is completely effective, as each type suffers from its own disadvantages. Moist wound therapy, for example, is known to promote fibroblast and keratinocyte proliferation and migration, collagen synthesis, early angiogenesis and wound contraction, but unfortunately all moist dressings cause fluid retention, and most of them require secondary dressings, making them difficult to use with exudative wounds. Bio-engineered tissue and artificial skin coverings are presently being researched and have not yet reached a state where they provide a true substitute for human skin. They also require surgical procedures to be used. Platelet-rich fibrin therapy utilizes techniques that process a patient's blood to isolate a fibrin or plasma that is rich in platelets, as well as growth factors that promote the natural healing process. Although promising, the technique is invasive and also is still, at present, being studied for safety and effectiveness. Lastly, negative pressure wound therapy uses a vacuum to remove excess fluid and cellular waste that usually prolong the inflammatory phase of wound healing. In spite of a very straightforward mechanism of action, there are many inconsistent results of negative pressure wound therapy studies.

Thus, a method of treating delayed wound healing associated with diabetes solving the aforementioned problems is desired.

SUMMARY OF THE INVENTION

The method of treating delayed healing of a wound associated with diabetes includes administering to the wound a composition comprising an anti-senescence compound and a pharmaceutically acceptable carrier. The anti-senescence compound may be 18α-Glycyrrhetinic acid, a Caveolin-1 (Cav-1) inhibitory compound, or a Polymerase I Transcript Release Factor (PTRF-1) inhibitory compound. The anti-senescence compound may be effective in preventing and/or reversing premature cellular senescence. The anti-senescence compound may be effective in promoting healing of a wound, e.g., a delayed or incompletely healed wound. The anti-senescence compound may be effective in promoting healing of a delayed healing wound or chronic wound of a diabetic patient, such as a diabetic ulcer or venous ulcer.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
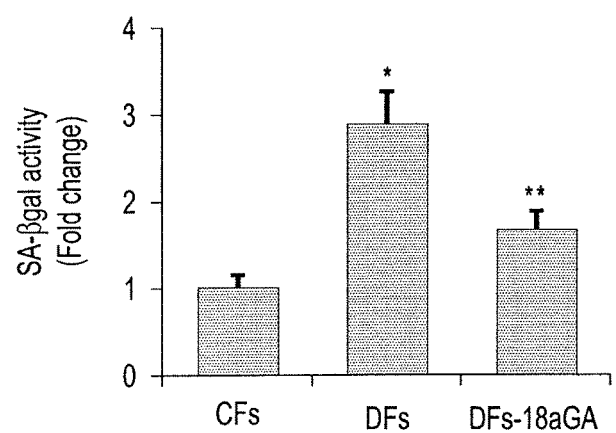
FIG. 1 is a graph showing SA-β-gal activity of control fibroblasts (CFs), diabetic fibroblasts (DFs), and diabetic fibroblasts treated with 18α-glycyrrhetinic acid (DFs-18aGA).

The method of treating delayed healing of a wound associated with diabetes includes administering to the wound a composition comprising an anti-senescence compound and a pharmaceutically acceptable carrier. The wound may be induced by diabetes, e.g., diabetes induced cellular senescence. The anti-senescence compound may be 18α-Glycyrrhetinic acid, a Caveolin-1 (Cav-1) inhibitory compound, or a Polymerase I Transcript Release Factor (PTRF-1) inhibitory compound. The anti-senescence compound may be effective in preventing and/or reversing premature cellular senescence. In particular, the anti-senescence compound may be effective in bringing about a significant decrease in one or more features of cellular senescence (e.g., the increased expression of SA-β-gal; decreased production of cyclin D1, phosphorylated RB, and growth factors; and increased level of p21). The anti-senescence compound may be effective in promoting healing of a wound, e.g., delayed or incompletely healed wound. The anti-senescence compound may be effective in promoting healing of a delayed healing wound or chronic wound of a diabetic patient, such as a diabetic ulcer or venous ulcer.

Previous studies by the present inventors have demonstrated that cultured fibroblasts of type 2 diabetes (DFs) are associated with a heightened state of oxidative stress, exemplified by increased ROS generation and decreased antioxidant capacity. This phenomenon is known to induce premature senescence in primary cells and tissues.

The present inventors have now determined that cellular senescence is a characteristic feature of the diabetic state. Using in vitro cultured dermal fibroblasts and in vivo circular wounds, the underlying mechanism mediating diabetes-induced cellular senescence and non-healing ulcers was studied by the present inventors. The present inventors found that the total antioxidant capacity and the expression of several Nrf2-dependent antioxidant enzymes were markedly decreased in fibroblasts from patients with type 2 diabetes (DFs, or diabetic fibroblasts). Similarly, it was also found that the nuclear accumulation of Nrf2 and its binding to the antioxidant response element (ARE) contained within the regulatory regions of so called "safeguard" genes (e.g., heme oxygenase and glutamate cysteine ligase) were also diminished due to diabetes in the patient. Consistent with these findings of shifts in favor of excessive reactive oxygen species (ROS), DFs were also found to display a significant increase in senescence-associated β-galactosidase activity and phospho-γ-histone H2AX (pH2AX) levels. Further, the ability of platelet-derived growth factor (PDGF) to promote cell proliferation/migration and to regulate the phosphorylation-dependent activation of protein kinase B (also referred to as "Akt") and extracellular signal-regulated kinases 1 and 2 (ERK1/2) was found to be attenuated due to diabetes in the patient.

The present inventors determined that diabetes-induced oxidative stress up-regulated the expression of PTRF, along with expression of its companion, Cav-1, which, in turn, sequestered Mdm2 away from p53. This process resulted in the activation of a p53/p21-dependent pathway and the induction of premature cellular senescence in DFs. The oxidative stress and senescence-based features observed in DFs were studied and found in a 10-day-old diabetic wound.

Figure 4:
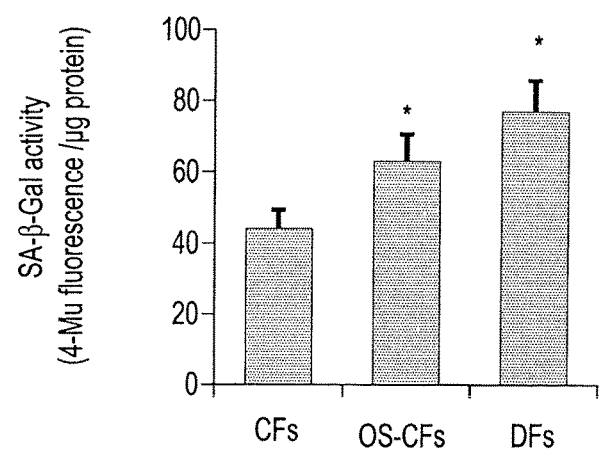
FIG. 4 is a graph showing SA-β-gal activity of control fibroblasts (CFs), control fibroblasts exposed to hydrogen peroxide (OS-CFs), and diabetic fibroblasts (DFs).
Figure 5:
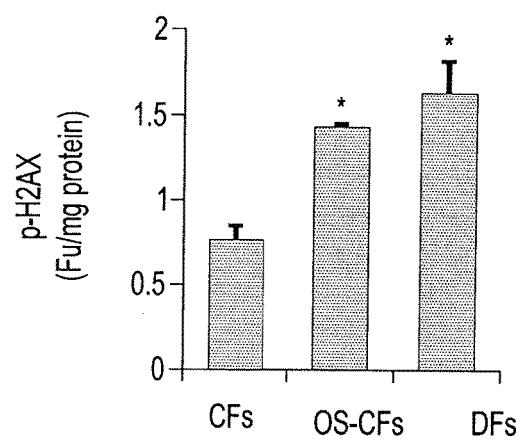
FIG. 5 is a graph showing p-H2AX contents of control fibroblasts (CFs), control fibroblasts exposed to hydrogen peroxide (OS-CFs), and diabetic fibroblasts (DFs).

It is noteworthy that the findings of the present inventors regarding the changes in PTRF/Cav-1 dynamics are not unique to the diabetic state, since similar findings were confirmed in oxidatively stressed control fibroblasts or OS-CF cell line (FIGS. 4 and 5).

The composition comprising the anti-senescence compound may be administered by any means suitable for delivery of the specific anti-senescence compound being utilized. The composition may be applied locally directly to the wound, for example, by way of injection directly into the wounded tissue or by way of application of a topical formulation containing the anti-senescence compound. Non-limiting examples of suitable local or topical formulations include sprays, liquids, gels, creams, ointments, transdermal patches and wound dressings.

Suitable pharmaceutically acceptable carriers or vehicles include any of those commonly used for topical administration. Preferably, the pharmaceutically acceptable carrier or vehicle includes pluronic acid.

An amount of the anti-senescence compound effective to promote wound healing may be determined initially from in vitro and/or in vive assays described herein and adjusted for specific desired anti-senescence compounds using routine methods. The composition may include, for example, a concentration of about 15 to about 75 µM of the anti-senescence compound.

Studies conducted by the present inventors confirmed that premature senescence in diabetic fibroblasts (DFs) and chronic oxidative stress fibroblasts (OS-CFs) can be reversed by counteracting a heightened state of oxidative stress using the Nrf2 activator 18α-glycyrrhetinic acid (GA). Specifically, Cav-1 and PTRF expression may be reduced by activating nuclear factor (erythroid-derived 2)-like 2 (Nrf2). Nrf2 is a transcription factor that is encoded by the NFE2L2 gene in humans. The Nrf2 antioxidant response pathway is the primary cellular defense against the cytotoxic effects of oxidative stress. Among other effects, NFE2L2 increases the expression of several antioxidant enzymes.

18α-GA is an active triterpenoid metabolite of glycyrrhizin, abundantly present in licorice roots. 18α-GA appears to have anti-inflammatory, anti-bacterial, anticancer and anti-oxidant activities. The present inventors have found that 18α-GA may promote healing of wounds associated with type 2 diabetes. In order to target activation in Nrf2, an effective dosage of 18α-glycyrrhetinic acid (GA) may be delivered to a diabetic patient suffering from impaired wound healing. For example a composition including about 30 µM of 18α-GA and a pharmaceutically acceptable carrier may be applied to the wound every other day to promote healing of the wound.

Glycyrrhetinic acid (GA), also referred to as enoxolone or glycyrrhetic acid is a pentacyclic triterpenoid derivative of the beta-amyrin type. Pentacyclic triterpenoids (including oleanane, ursane and lupane groups) are commonly found in medicinal plants, such as in the *Glycyrrhiza* species, the *Gymnema* species, *Centella asiatica*, *Camellia sinensis*, the *Crataegus* species and *Olea europaea*. Although 18α-GA is described herein, other pentacyclic triterpenoid derivatives or pentacyclic triterpenoids may also be used.

Figure 2:
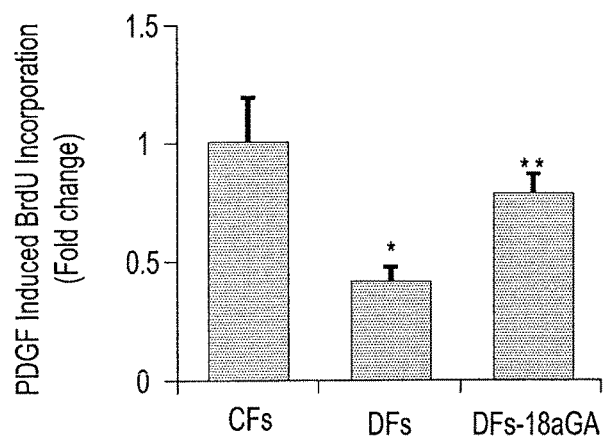
FIG. 2 is a graph showing BrdU incorporation into DNA of control fibroblasts (CFs), diabetic fibroblasts (DFs), and diabetic fibroblasts treated with 18α-glycyrrhetinic acid (GA) (DFs-18aGA).
Figure 3:
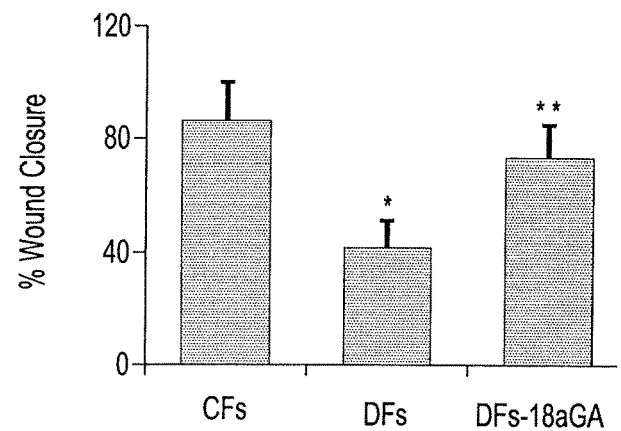
FIG. 3 is a graph showing rate of wound closure in control fibroblasts (CFs), diabetic fibroblasts (DFs), and diabetic fibroblasts treated with 18α-glycyrrhetinic acid (DFs-18aGA).

The findings of the present inventors demonstrate that DFs treated with 18α-GA expressed a significantly lower level of SA-β-gal (FIG. 1), and displayed an increased rate of proliferation (FIG. 2). When administered to a circular wound of a diabetic rat, a composition including 30 µM 18α-GA and pluronic acid was found to ameliorate impaired wound healing (FIG. 3).

The Cav-1 inhibitory compound may be effective in reducing expression levels of Caveolin-1 (Cav-1) at protein or mRNA levels in patients with diabetes in order to enhance healing of wounds in diabetic patients, particularly delayed healing or non-healing diabetic ulcers. The Cav-1 inhibitory compound can inhibit activity of a Cav-1 polypeptide per se, or can inhibit expression of one or more Cav-1 gene products. As specific examples, Cav-1 inhibitory compounds that inhibit expression of a Cav-1 gene product can inhibit transcription of a gene encoding Cav-1, thereby blocking synthesis of Cav-1 mRNA or translation of mRNA encoding Cav-1, thereby blocking synthesis of Cav-1 polypeptides. Compounds useful for inhibiting activity of a Cav-1 polypeptide per se include, e.g., small molecules, antibodies, polypeptides, polynucleotides, or other Cav-1 antagonists. Compounds useful for inhibiting expression of Cav-1 gene products include, by way of example and not limitation, antisense, siRNA (small interfering RNA, i.e., short double-stranded RNA molecules that can be used to interfere with expression of genes with complementary nucleotide sequences by causing mRNA to be broken down after transcription, thereby preventing translation) and miRNA (micro RNA, i.e., small non-encoding RNA molecules that regulate gene expression by complementary base-pairing with nucleotide sequences of mRNA, preventing translation of proteins) oligonucleotides or polynucleotides. The Cav-1 inhibitory compound may be an antisense oligonucleotide or an siRNA. The antisense oligonucleotide may be a Morpholino antisense oligonucleotide.

Figure 12:
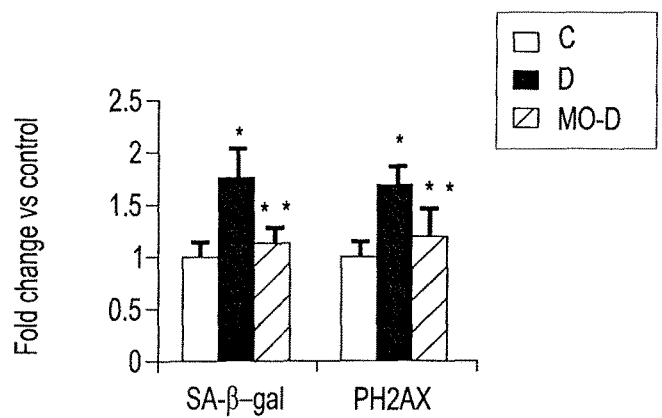
FIG. 12 is a graph showing SA-β-gal activity and PH2AX contents in Control (C), Diabetic (D), and Morpholino treated diabetic wounds of rats (MO-D).
Figure 13:
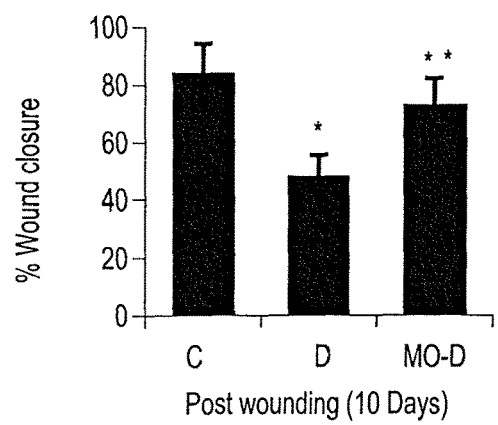
FIG. 13 is a graph showing rate of wound closure in Control (C), Diabetic (D) and Morpholino treated diabetic wounds of rats (MO-D)

As discussed in detail below, the findings of the present inventors demonstrate that Cav-1 siRNA-treated DFs expressed a significantly lower level of SA-β-gal (FIG. 6) and p53, and displayed an increased rate of proliferation (FIG. 7) and migration (FIG. 8) and enhanced responsiveness to mitotic agents. Furthermore, Morpholino Cav-1 based antisense therapy ameliorated impaired wound healing in vivo in type 2 diabetes (FIGS. 12-13).

As described previously, the anti-senescence compound of the present composition may be a PTRF-1 (polymerase 1 transcript release factor) inhibitory compound. The PTRF-1 inhibitory compound may be effective in reducing expression levels of PTRF-1 at protein or mRNA levels in patients with diabetes in order to enhance healing of wounds in diabetic patients, particularly delayed healing or non-healing diabetic ulcers. The PTRF-1 inhibitory compound may inhibit an activity of a PTRF-1 polypeptide per se, or may inhibit expression of one or more PTRF-1 gene products. As specific examples, PTRF-1 inhibitory compounds that inhibit expression of a PTRF-1 gene product can inhibit transcription of a gene encoding PTRF-1, thereby blocking synthesis of PTRF-1 mRNA, or translation of mRNA encoding a PTRF-1, thereby blocking synthesis of PTRF-1 polypeptides. Compounds useful for inhibiting an activity of a PTRF-1 polypeptide per se include, for example, small molecules, antibodies, polypeptides, polynucleotides, or other PTRF-1 antagonists. Compounds useful for inhibiting expression of PTRF-1 gene products include, for example, antisense, siRNA and miRNA oligonucleotides or polynucleotides. The PTRF-1 inhibitory compound may be an antisense oligonucleotide or a siRNA. The antisense oligonucleotide may be a Morpholino antisense oligonucleotide.

Figure 9:
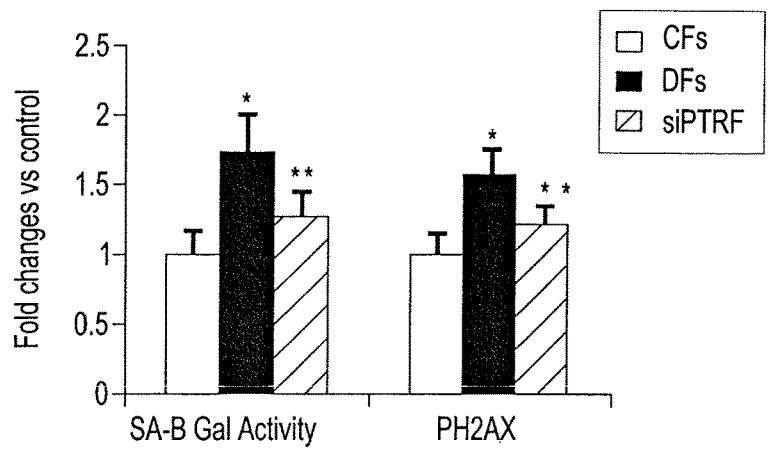
FIG. 9 is a graph showing SA-β-gal activity and PH2AX contents in CFs, DFs, and DFs with PTRF knocked down using an siRNA based technique (siPTRF).

As discussed in detail below, the findings of the present inventors demonstrate that PTRF siRNA-treated DFs expressed a significantly lower level of SA-R-gal (FIG. 9) and p53 (FIG. 10), and displayed an increased rate of proliferation (FIG. 11) and migration and enhanced responsiveness to mitotic agents.

As mentioned previously, delayed wound healing in a subject may be ameliorated by the targeted depletion of Cav-1 or PTRF using siRNA- or Vivo-Morpholino antisense-based gene therapy. The targeted depletion of Cav-1 or PTRF may inhibit diabetes/oxidative stress-induced premature senescence and accelerate the tissue repair mechanism in this disease state.

Many age-related diseases appear to stem from the progressive, irreversible accumulation of oxidatively damaged macromolecules. At the cellular level, exposure to tetra-butyl hydroperoxide, HP or hyperbaric atmosphere with high oxygen partial pressure produces a growth arrest that is indistinguishable from that observed during replicative senescence. The findings of the present inventors indicate that reduced resistance to ROS may lead to oxidative damage, and eventually to growth arrest and cellular senescence. As described herein, at earlier PDLs than their normal counterparts, DFs exhibited a number of senescence-based features, including the increased expression of SA-β-gal, a reduced rate of growth/DNA synthesis and hypo-responsiveness to the mitotic effect of growth factors and serum. The aforementioned proposition is consistent with the findings that DFs accumulate large amounts of oxidative by-products, such as pH2AX/β-OHdG/protein-bound carbonyls, in addition to the increased activity/expression of NADPH oxidase, a severe exhaustion of the intracellular antioxidant defenses and ultimately more senescent cells in response to repetitive HP treatment. It is noteworthy that the heightened state of oxidative stress and cellular senescence in DFs are apparently associated with a marked enhancement in the p53/p21 tumor suppressor pathway.

The findings of the present inventors confirm that Cav-1 protein expression was upregulated in DFs. Cav-1 is the major structural component of caveolae, and it appears to exert a variety of biological functions, including the regulation of cholesterol levels, vascular transport, proliferation and apoptosis in a variety of cell types. This molecule has been implicated as a modulator of oxidative stress and cellular senescence. In this context, the overexpression of Cav-1 protein promotes G1 arrest and premature senescence by a p53/p21-dependent mechanism.

Cav-1 has been identified as a novel gene that regulates replicative senescence and SIPS. The present inventors have determined that Cav-1 is linked to the progression of cellular senescence and impaired wound healing in diabetes. Dermal fibroblasts and wounded tissues from rats with type 2 diabetes were found to exhibit increased ROS generation and decreased antioxidant capacity. When cellular senescence and the upstream signaling pathway of Cav-1 as a function of diabetes was assessed using in vitro and in vivo models of wound healing, Cav-1 was identified as a novel signaling player that links oxidative stress to the impairment of wound healing in diabetes. As such, cellular senescence stemming from the oxidative stress-mediated overexpression of Cav-1 was found to constitute a mechanism for the development of non-healing diabetic ulcers.

As described herein, fibroblasts of type 2 diabetes (DFs) display senescence features when grown in culture. In this context, DFs revealed the following characteristics: (1) reduced rate of growth; (2) positive staining with the senescence marker β-gal and reduced responsiveness to the mitogenic effects of EGF, IGF-1 and serum; and (3) a flattened, large vacuolated cellular morphology. This senescence phenotype is accompanied by the overexpression of Cav-1/PTRF, the increased binding of Cav-1 to PTRF and Mdm2, the decreased affinity of Mdm2 for p53, and the activation of the p53/p21-dependent pathway. The targeted depletion of Cav-1 using siRNA- or Vivo-Morpholino antisense-based gene therapy markedly inhibited diabetes/oxidative stress-induced premature senescence and accelerated the tissue repair mechanism in this disease state.

Reduced resistance to ROS has been found to lead to oxidative damage and eventually to growth arrest and cellular senescence.

P53 stabilization, p21 upregulation and the induction of premature senescence were dramatically inhibited in DFs that had been treated with anti-Cav-1 siRNA. As Cav-1 overexpression is a key element in promoting cellular senescence during diabetes, DFs harboring Cav-1 siRNA display phenotypic features that are similar to their control counterparts. The findings of the present inventors demonstrate that Cav-1 siRNA-treated DFs expressed a significantly lower level of SA-β-gal and p53/p21, displayed an increased rate of proliferation and migration and enhanced responsiveness to mitotic agents. Increased Cav-1 expression in DFs activates p53/p21 signaling, a principle instigator of SIPS.

The aforementioned key players of cellular senescence in diabetes in the context of Mdm2, a negative p53 regulator and a target molecule for the Cav-1 binding motif of p53 were assessed. Although the total Mdm2 protein level was not altered in DFs, the degree of binding to Cav-1, which was assessed using co-immunoprecipitation, was higher in DFs when compared to their corresponding control values. These findings are consistent with previous reports showing that during oxidative stress-induced senescence, Mdm2 is neutralized by Cav-1, thus leading to p53 stabilization. Cav-1 upregulation, induced by the heightened state of oxidative stress in diabetes, sequesters an increased amount of Mdm2. As a result, a decrease in the proteosomal degradation of p53, together with the concomitant activation of p21 (a downstream target of p53 that is responsible for cell-cycle arrest), may ensue, thus eventuating in the induction of premature senescence in DFs. The present inventors have found that p53 stabilization, p21 upregulation and the induction of premature senescence were dramatically inhibited in DFs that had been treated with anti-Cav-1 siRNA.

Although Cav-1 is known to be a key player in SIPS induction, little information is available regarding the upstream molecules involved in the overexpression of this scaffolding protein constituent of caveolae in diabetes. The studies of the present inventors demonstrated that the inhibition of p38, but not PI3K-Akt, JNK or the ERK1/2-dependent pathway, abolished the diabetes-induced Sp1-mediated upregulation of Cav-1 protein expression and SIP development. More importantly, the present inventors also identified a significant elevation in the level of p38 under basal conditions and in response to HP treatment. These data are reminiscent of those previously reported confirming that the activation of p38 by a sublethal dose of HP induced premature senescence in normal cells, but not in cells lacking caveolin-1. Moreover, the p38 MAPK-dependent increased phosphorylation of Cav-1 on tyrosine 14 in response to oxidative stress further supports the idea that this MAPK may regulate Cav-1 at the transcriptional and post-translational levels.

A 9-day-old circular wound in diabetic rats was ameliorated partially or fully by the application of the Vivo-Morpholino-Cav-1 based antisense therapy. Because it is abundant in almost every cell type in wounds, including fibroblasts, endothelial cells, macrophages, neutrophils, and epithelial cells, Cav-1 plays a crucial role in the pathogenesis of impaired wound healing in diabetes. Non-healing diabetic ulcers are a major cause of morbidity and contribute to the use of healthcare resources. A recent statistic revealed that 60% of non-traumatic, lower-limb amputations occur in diabetic patients. The underlying mechanism of this phenomenon is still poorly understood, and therapeutic options are limited. Based on the findings of the present inventors in fibroblasts, which are considered to be repair-committed cells, wound healing impairment in diabetics in the context of Cav-1 signaling and cellular senescence was studied. The data revealed that as in DFs, the Cav-1 level, degree of Cav-1 binding to Mdm2/PTRF, and the activities of SA-β-gal, pH2AX and the p53/p21-dependent pathways were all increased in a 9-day-old circular wound in diabetic rats. In contrast, the binding of Mdm2 to p53 appear to be suppressed as a function of diabetes. Intriguingly, and potentially important therapeutically, the present inventors confirmed that most of the aforementioned abnormalities were ameliorated partially or fully by the application of the Vivo-Morpholino-Cav-1 based antisense therapy.

Cav-1 is a key player of a novel signaling pathway that links a heightened state of oxidative stress to cellular senescence and impaired wound healing in diabetes. ROS induces the premature senescence of fibroblasts (and possibly other cells) within the wound (e.g., endothelial cells, epithelial cells, and macrophages) in a caveolin-1/Mdm2/p53-p21-dependent manner, and these senescent cells contribute to the pathogenesis of non-healing diabetic wounds. To this end, therapeutic intervention aimed at reducing Cav-1 expression within the wound microenvironment may be effective to treat or prevent chronic, non-healing ulcers. However, because Cav-1 is considered to be a tumor suppressor in certain forms of cancer, indiscriminate down-regulation of Cav-1 expression may accelerate the healing process, but increase the chance of tumor development. Accordingly, a targeted-knock down of Cav-1 expression as described herein may represent a strategic approach for a mechanism-based therapy of diabetic ulcers.

DFs and OD-CFs displayed senescence-like features and a reduction in the maintenance of cellular redox balance. DFs showed a marked enhancement in SA-β-gal expression (FIG. 4), increased DNA damage foci accompanied by histone pH2AX phosphorylation (FIG. 5) and growth inhibition. The latter process was illustrated by assessing two biological cell proliferation markers, including the rate of cell doubling per day and BrdU incorporation, a measure of the rate of DNA synthesis. Moreover, the expression of p53 and p21, key regulators of cellular senescence, were also upregulated in DFs when compared to their control counterparts. Interestingly, these phenotypic features of senescence in DFs were associated with an aberration in the systems that are involved in reductive biosynthesis (NADPH/NADP+), maintenance of the cellular redox balance and ROS scavenging (e.g., mRNA levels of G6PD and thioredoxinreductase). Consistent with these data, it was found that in DFs, a significant reduction in total antioxidant capacity in-situ, quantified using a Trolox-based assay.

To gain insight into whether the decreased resistance to oxidative stress could explain the premature onset of cellular senescence in DFs, the tendency of these cells and their control counterparts to undergo changes in senescence-based biomarkers in response to a sublethal dose (150 µM) of hydrogen peroxide (HP) was compared. During the first cycle of HP treatment, DFs exhibited an increase in SA-β-gal activity and the level of pH2A.X at PDL 35, a phenomenon that was not apparent in CFs (data not shown). Similarly, the aforementioned paradigm also negatively affected the redox/antioxidant network in diabetic fibroblasts, but not control fibroblasts. It is noteworthy that CFs exposed to a paradigm of chronic oxidative stress (OS-CFs) recapitulated most of the senescence-based features observed in DFs. Together, these data support the premise that DFs with an altered redox balance and increased oxidative damage have a higher propensity for stress-induced cellular senescence. The above findings regarding DFs and OS-CFs are reminiscent of those reported previously in G6PD- and Gpx1-deficient fibroblasts.

Cav-1 overexpression contributes to cellular senescence in DFs. An accumulation of senescent cells may arise from the enhanced expression of factors controlling oxidative stress-mediated cellular senescence, such as CCN1 (CYR61), plasminogen activator inhibitor-1 or Cav-1. Cav-1 has been shown to play a key role in replicative and stress-induced premature senescence (SIPS). A sublethal dose of HP has been shown to increase endogenous Cav-1 expression and induced premature senescence in NIH 3T3 cells. As indicated above, DFs are more sensitive to HP and exhibit a state of heightened oxidative stress. Accordingly, the Cav-1 signaling pathway in the context of diabetes and cellular senescence was examined by the present inventors. The data derived from the studies of the present inventors confirmed that the Cav-1 level was markedly increased in DFs, compared to their control counterparts. In particular, diabetes-induced Cav-1 upregulation was found to be apparently associated with impaired PDGF ability to regulate the phosphorylation-dependent activation of Akt and ERK1/2. Other growth promoting polypeptides, including IGF-1 and EGF, also exhibited in DFs a similar pattern of effect to that seen with the PDGF (data not shown). The data derived by the present inventors are consistent with previous reports indicating that Cav-1 may bind to and negatively regulate EGF and PDGF receptors.

Further experiments were conducted by the present inventors to examine the impact of the attenuation in growth factor signaling on key fibroblast functions essential for wound healing, including cell proliferation and cell migration. The proliferation index, as exemplified by the incorporation of BrdU and the cell cycle profile, was assessed by exposing starved cultured fibroblasts to mitotic growth factors or to serum. Because the stimulation potency of these factors varies, a dose-response ELISA for BrdU incorporation was established for each factor, and the dose providing the maximum response was selected. In serum-induced proliferating cells in CFs, the optical density at 450 nm (OD450) was more than 10-fold higher than that observed for starved cells. Similarly, PDGF, EGF and IGF also increased the proliferation rate by approximately 10-fold, 7.1-fold and 6.7-fold, respectively. This stimulatory action of the growth factors on cell proliferation was markedly suppressed in diabetic conditions. To further dissect the mechanisms underlying growth-rate inhibition, the cell cycle profile was analyzed using a flow cytometry-based technique. In response to PDGF, DFs showed lower propensity for S-phase entry and an increased number of cells arrested in G0/G1 when compared to corresponding control values.

Cell migration is an additional parameter related to tissue regeneration. Cell migration was examined in cultured fibroblasts in response to a mechanical wound. Fibroblasts in monolayer culture were subjected to mechanical scratch wound injury model in the presence or absence of PDGF, IGF-1 and EGF or serum. The number of cells that migrated into the cell-free wound zone over the course of 24 hrs post-injury in CFs was markedly increased in response to these growth factors, with PDGF being the most potent among them. This phenomenon was reduced by approximately 50% in DFs when compared to the corresponding control values. Intriguingly, the unresponsiveness of DFs to the aforementioned growth-promoting polypeptides in terms of cell signaling and cell proliferation/migration was recapitulated in CFs subjected to a chronic paradigm of oxidative stress.

Gain-of-function and loss-of-function strategies in control and type 2 diabetic fibroblasts were considered. To examine whether a cause and effect relationship exists between the over-expression of Cav-1 and the phenotypic features of diabetes-induced cellular senescence, a loss- and gain-of-function genetic strategy was instituted. In this regard, the present inventors found that CFs overexpressing Cav-1 (CFs-pCMV-Cav-1) exhibited a marked increase in the activity of β-SA-gal (FIG. 6) when compared to their corresponding vector-treated (CFs-pCMV-GRP) control values. CFs overexpressing Cav-1 (CFs-pCMV-Cav-1) also exhibited a marked increase in pH2AX contents and levels of p53 and p21 when compared to their corresponding vector-treated (CFs-pCMV-GRP) control values. In contrast, the activity of Akt and the rates of cell proliferation (FIG. 7) and migration (FIG. 8) in response to PDGF were attenuated at a high cellular Cav-1 level. A subset of the above data has been previously reported in human diploid fibroblasts and in mouse embryonic fibroblasts.

Figure 6:
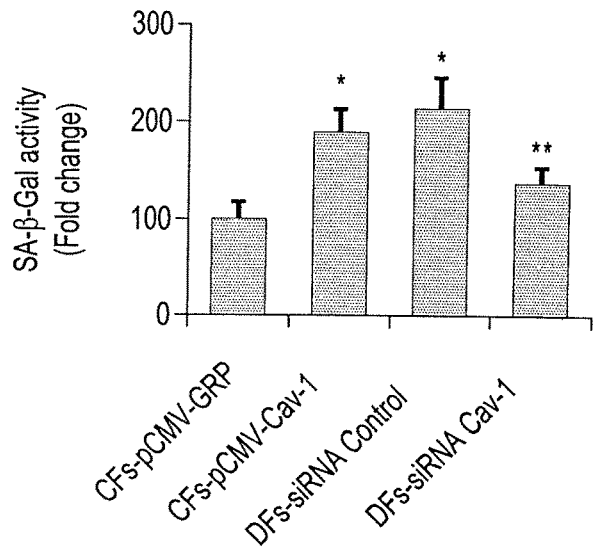
FIG. 6 is a graph showing SA-β-gal activity of CFs transfected with caveolin-1-pCMV(CFs-pCMV-Cav-1), its vector control (CFs-pCMV-GRP), DFs, and DFs rendered caveolin-1 deficient (DFs-siRNA Cav-1) using siRNA-based technique.
Figure 7:
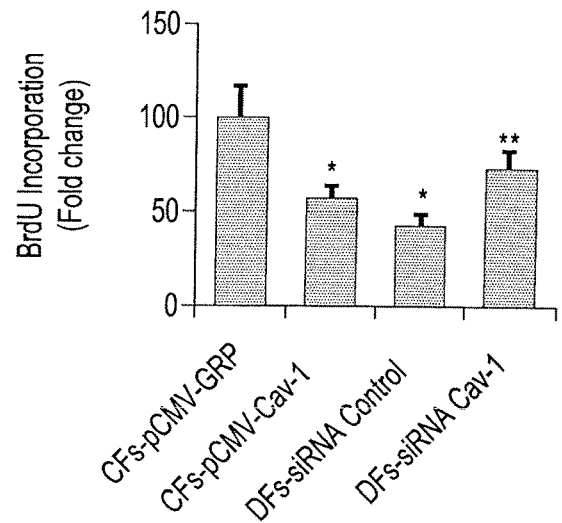
FIG. 7 is a graph showing BrdU incorporation into DNA of CFs transfected with caveolin-1-pCMV(CFs-pCMV-Cav-1), its vector control (CFs-pCMV-GRP), DFs, and DFs rendered caveolin-1 deficient (DFs-siRNA Cav-1) using siRNA-based technique.
Figure 8:
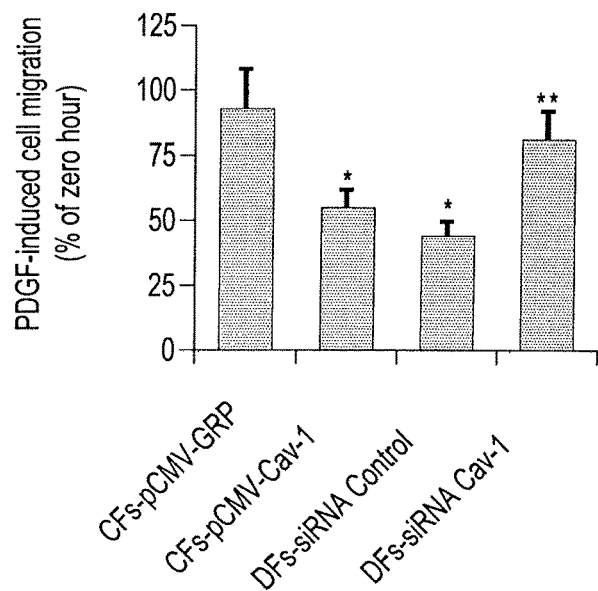
FIG. 8 is a graph showing PDGF-induced cell migration for CFs transfected with caveolin-1-pCMV(CFs-pCMV-Cav-1), its vector control (CFs-pCMV-GRP), DFs, and DFs rendered caveolin-1 deficient (DFs-Cav-1 siRNA) using siRNA-based technique.

The present inventors have determined that knocking down Cav-1 with siRNA in DFs can exert a beneficial effect with respect to cellular senescence and the defect in PDGF actions. The tendency of the diabetic state to induce premature senescence, as reflected by the increase in SA-β-gal activity, was found to be reduced in cells harboring the Cav-1 siRNA (FIG. 6). The tendency of the diabetic state to induce premature senescence, as reflected by the increase in the levels of pH2AX, p53, and p21 was also found to be reduced in cells harboring the Cav-1 siRNA. Consistent with these findings, reducing Cav-1 level in DFs using the siRNA-based technique partially restored PDGF responses, as exemplified by the increased phosphorylation of p-Akt and the enhanced rates of cellular proliferation (e.g., DNA synthesis) (FIG. 7) and migration (FIG. 8). Overall, the data obtained by the present inventors supports the notion that cellular senescence (e.g., level/activity of SA-β-gal, pH2AX, p53, p21) and decreased rates of cell proliferation and migration in DFs may stem, at least in part, from Cav-1 overexpression. More intriguingly, a functional recovery of DFs, in terms of growth factor responsiveness, appears to be attainable by instituting a therapeutic strategy that reduces the Cav-1 level.

Figure 10:
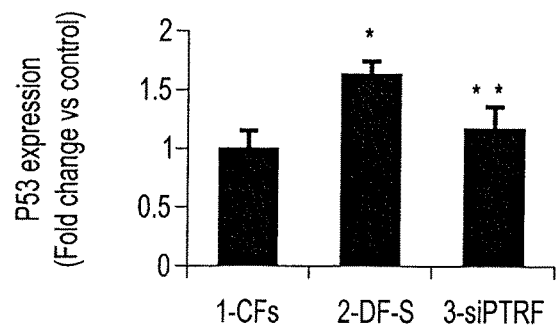
FIG. 10 is a graph showing the expression of p53 in CFs, DFs and siPTRF.
Figure 11:
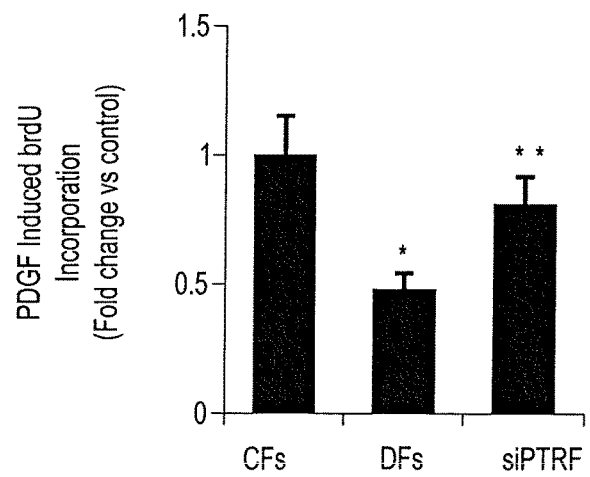
FIG. 11 is a graph showing BrdU incorporation into DNAs of CFs, DFs, and siPTRF.

Cav-1 overexpression in DFs induces cellular senescence through a mechanism involving Mdm2/PTRF-dependent signaling. To investigate the molecular mechanism(s) underlying cellular senescence and the activation of p53-p21 signaling as a function of diabetes, the present inventors focused on the PTRF-Cav-1-Mdm2-dependent pathway. Both PTRF and Cav-1 are co-localized within the caveolae, involved in the sequestration of Mdm2 (an ubiquitin ligase which targets p53 for degradation), and have been shown to be elevated during replicative senescence and oxidative stress-induced cellular senescence. PTRF/Cavin-1 and Mdm2 expression were measured in total cell lysates by Western blotting. Protein expression of PTRF was markedly increased in DFs when compared to their corresponding control values. A co-immunoprecipitation-based assay was used to assess the interaction of caveolin-1 with PTRF and Mdm2, as well as the binding of p53 to Mdm2. Co-immunoprecipitation studies in DFs demonstrated a significant enhancement in the binding of PTRF to Cav-1, and also of Cav-1 to Mdm2. PTRF in DFs was knocked down using an siRNA-based technique, and 48 to 72 hours afterward, the cells were used for the assessment of SA-β-gal activity/pH2AX contents (FIG. 9), the expression of p53 (FIG. 10) and the effects of PDGF on cell proliferation/migration (FIG. 11). The siRNA sequences were designed and synthesized by Qiagen (USA), catalogue number S102655450. The binding affinity of p53 for Mdm2 was markedly suppressed as a function of diabetes. The current findings suggest a sequence of events in which a heightened state of oxidative stress in DFs upregulates PTRF/cavin-1 protein expression, which, in turn, promotes the membrane localization of Mdm2 and its interaction with the already overexpressed Cav-1. This increase in the sequestration of Mdm2 by Cav-1 in DFs activates the p53/p21-dependent pathway, with the concomitant induction of cellular senescence. Support for the aforementioned proposition is best exemplified by data obtained by the present inventors showing that PTRF down-regulation in DFs via an siRNA-based strategy reduced not only the levels of SA-β-gal and pH2AX (FIG. 9) but also the activity of p53 (FIG. 10). Moreover, partial restoration of PDGF activity, viewed in the context of cell proliferation/migration and Akt phosphorylation, was also evident in the siRNA-PTRF-DFs (FIG. 11).

It is noteworthy that most of the data regarding the changes in PTRF/Cav-1 dynamics are not unique to the diabetic state, since similar findings were confirmed in OS-CF cell line.

An in vivo-morpholino-based knockdown of Cav-1 ameliorated both premature senescence and impaired wound healing in GK diabetic animals. Cellular senescence and an increased ROS level may contribute to impaired wound healing under various pathological conditions. The overexpression of Cav-1 has been shown to inhibit muscle repair mechanisms in cell culture studies and in vivo, whereas accelerated skin wound healing has been reported in cav-1-null mice. The current data clearly demonstrate that a heightened state of oxidative stress, the overexpression of Cav-1 and cellular senescence are characteristic features of DFs, a key cell involve in the reparative mechanism of the healing process. To gain insights that are pathologically and clinically relevant, the effect of the diabetic state on key biomarkers of cellular senescence and oxidative stress were assessed, as well as the interaction between Cav-1-PTRF and Mdm2 over the course of cutaneous wound healing. Activities of SA-β-gal and pH2AX were enhanced in 9-day-old diabetic wounds. Similarly, the levels of key molecules within the Cav-1-dependent signaling, including Cav-1, PTRF, p53, and p21 were also up-regulated as a function of diabetes. Consistent with the aforementioned abnormalities, diabetic wounds displayed a significant alteration in Cav-1 dynamics, exemplified here by the increase in the binding of Cav-1 to Mdm2 and PTRF, in addition to a reduction in the interaction between Mdm2 and p53.

Whether a heightened state of oxidative stress, the constant companion of senescence, represents a characteristic feature of a 9-day diabetic wound was assessed by determining key molecules in the pro-oxidant-antioxidant-antioxidant network. The resulting data confirmed that NADPH oxidase activity and the mRNA level of its subunit, NOX1, were enhanced in the 9-day diabetic wound. In contrast, the in situ total antioxidant capacity, the ratio of NADPH/NADP, and the mRNA levels of expression of antioxidant enzymes (e.g., TR, G6PD) were reduced as a function of diabetes. In aggregates, these findings are in harmony with the premise that chronic oxidative stress activates the Cav-1 dependent signaling, and this, in turn, contributes, at least in part, to the senescence-based features of non-healing diabetic wounds.

A cause-and-effect relationship indeed exists between the up-regulation of Cav-1-dependent signaling, cellular senescence and impaired wound healing in diabetes. In vivo Morpholino Cav1-based antisense therapy was applied to a diabetic circular skin wound using pluronic acid as a vehicle. This novel wound-based knockdown strategy ameliorated the diabetes-related increase in wound contents of SA-β-gal/pH2AX (FIG. 12), Cav-1, PTRF, p53 and p21. Moreover, the enhanced binding of Cav-1 to Mdm2 and PTRF and the decreased affinity of Mdm2 for p53 in a 9-day diabetic wound was also restored almost to normal values in response to the vivo-Morpholino treatment. The above beneficial effect of Cav-1 knockdown in diabetic wounds was not limited to the senescence and Cav-1 signaling pathway, but extended also to the heightened state of oxidative stress. In this connection, total antioxidant capacity, the ratio of NADPH/NADP, and the level of expression of G6PD and TR were increased in MO-D when compared to corresponding vehicle-treated diabetic wounds. These data regarding the antioxidant capacity are of interest, especially when viewed in the context of the findings showing that overexpression of Cav-1, like that of diabetes, suppressed the activity of Nrf2 and its associated phase 2 dependent antioxidant enzymes. The most intriguing and novel finding, however, lies in the fact that delayed healing in diabetic wounds can be ameliorated by a genetic knockdown of Cav-1 (FIG. 13). FIGS. 12-13, respectively, summarize data obtained regarding diabetes-related increase in wound contents of SA-β-gal/pH2AX and rate of wound healing assessed using a 10-day control wound (C), diabetic wound (D) and vivo-Morpholino-treated diabetic wound (MO-D).

The overexpression of Cav-1, possibly stemming from a state of heightened oxidative stress, contributes, at least in part, to the underlying mechanisms of cellular senescence and impaired wound healing in diabetes.

The following examples illustrate the present teachings. The following describes the experimental procedures used in the examples that follow.

Cell culture and HP treatment. Primary dermal fibroblasts cell lines were established from the dorsal skin of female GotoKakizaki (GK; age 12-15 months) rat, a model for non-obese type 2 diabetes (DFs) and their Wistar control counterparts (CFs). Briefly, the dermis was cut into small pieces and incubated in Dulbecco's modified Eagle medium (DMEM; Invitrogen) containing collagenase (250 U/ml; Sigma) for 30 minutes at 37° C. in 5% CO2 with constant agitation. The sections were triturated vigorously to release fibroblasts, and these cells were collected by centrifugation. The resulting pellet was washed twice with phosphate buffered saline (PBS), resuspended in complete medium (DMEM supplemented with 10% fetal calf serum, penicillin [100 U/ml], streptomycin [100 μg/ml], 2 mM glutamine, and 10 mM HEPES) and was then cultured under standard conditions.

Oxidatively-stressed CFs (OS-CFs). A heightened state of oxidative stress and premature senescence in CFs were induced using hydrogen peroxide (HP) as a stressor. The HP treatment was conducted by seeding approximately $1 \times 10^6$ cells in a T75 tissue culture flask. Twenty-four hours later, the cells were exposed to a sublethal dose of HP (150 μM) for 2 hours, washed 2x with PBS and after 4 days of culturing in HP free medium; they were split in a 1:2 ratio, and then the aforementioned protocol was repeated again for cells receiving the second and third HP treatment. A third passage HP-treated CFs denoted in the current study as (OS-CFs) together with the corresponding CFs and DFs were used in most of the assays outlined below.

Senescence-associated β-galactosidase staining and quantification assays. The senescence-associated β-galactosidase (SA-β-gal) activity was determined using a senescence β-gal staining kit (Cell Signaling Technology). The experiments were performed in six-well plates following the instruction of the manufacturer. Cells were washed 3x with PBS, fixed for 3 min at room temperature in 3% formaldehyde, washed and then incubated overnight at 37° C. without CO2 in a freshly prepared staining medium [1 mg/ml 5-bromo-4-chloro-3-indolyl-β-D-galactopyranoside (X-gal), 40 mM citric acid/sodium phosphate, pH 6.0, 5 mM potassium ferricyanide, 150 mm NaCl, 2 mM MgCl2] (Debacq-Chainiaux et al., 2009). Cells were then examined for blue-green staining of cytoplasm indicative of senescence. For a prices quantification of β-gal activity, the rate of conversion of 4-methylumbelliferyl-3-D-galactopyranoside to the fluorescence hydrolyzed product 4-methylumbellifrone at pH 6 was assessed using previously published procedure (Gary and kindell 2005).

PH2AX immune-fluorescence-staining and quantification assay. Phosphorylation of H2AX at serine 139 (pH2AX), a sensitive marker for cellular senescence and DNA damage, was evaluated using either an immune-fluorescence staining or a fluorometric-based assay kit (Active Motif, USA). Briefly, cells derived from various experimental groups were cultured on cover slips for 24 hrs, then washed (PBS), fixed (4% paraformaldehyde, 10 min), permeabilized (0.3% Triton X-100, 10 min), blocked (2% BSA, 1 hr) and incubated with H2AX phosphorylated at serine 139 overnight at 4° C. After the samples were rinsed with PBS, the coverslips were incubated for 1 hr in the dark with the secondary goat-ant-rabbit conjugated to Texas Red (Invitrogen, USA). Samples were mounted with Vectashield mounting medium for fluorescence with DAPI (Vector Lab, USA). Immunofluorescence microscopy was performed using a Zeiss Confocal microscope (Carl Zeiss, Germany). A fluorometric-based assay kit (Active Motif) was used to quantitatively assess the level of pH2AX. Cells or wounded tissues were sonicated in SDS lysis buffer and the DNA fragments were confirmed to be within 100-1000-bp. About 5 μg/ml anti-pH2AX was added to the lysates and allowed to incubate at 4° C. overnight. Thereafter, the samples were washed, incubated for 1 hr at room temperature with Alexis 488 goat anti-rabbit antibody and then the fluorescence was measured at about 485 nm excitation and 520 nm emission wavelengths using a fluorometer (Promega, USA).

Growth Rates. Control and diabetic fibroblasts were seeded at densities of $3 \times 10^4$ and $1 \times 10^4$ cells/ml, respectively, (N0) in DMEM supplemented with 10% FCS and antibiotics. Seeding at these concentrations gave approximately 50% confluence for both cell types. The cells were harvested at confluence (Nf), and their population doublings were estimated using the previously published formula (RCPD)=log 2(Nf/N0)/t, where t=time in days; Nf, cell number at the time of passage and N0, cell number at the time of seeding (Schneider and Epstein, 1972). The data are expressed as the mean growth rate over 6-9 passages of cell growth.

Cell-cycle analysis and synchronization. Cells at 70-80% confluence were washed with PBS, detached with a trypsin/EDTA solution and fixed with 70% ethanol for 30 min. After washing with PBS, the fixed cells were incubated with RNAase A for 30 min at 37° C., resuspended in 0.5 ml PBS, stained with propidium iodide in the dark for 30 minutes and then analyzed using a FACScan equipped with a Xe/Ne laser at 488 nm. To promote cell cycle synchronization, the cells were rendered quiescent by serum deprivation for 48 hours, and this step was followed by the addition of PDGF to stimulate the cells to re-enter the cell cycle. The cell populations in the G1, S and G/M phases were quantified after 24 hours of PDGF stimulation.

Assessment of key fibroblast functions essential for wound healing. To assess cell proliferation, fibroblasts were seeded into a 96-well plate at a density of $1 \times 10^4$ per well and were allowed to adhere overnight in DMEM medium supplemented with 10% FCS. After arrest by incubation in serum-free medium for 24 hours, the cells were exposed to growth factors, and the incorporation of bromodeoxyuridine (BrdU) into DNA was determined using the manufacturer's protocol (Roche Diagnostics). Similarly, for the in vitro wound (migration) experiments, cultured fibroblasts were grown in six-well plates until they reached confluence. The medium was removed, the cells were washed with PBS 3× before culturing was continued in serum-free DMEM containing 0.5% BSA for an additional 24 hours. Thereafter, the monolayer was artificially wounded by using a pipette tip to scratch across the plate; the cells were washed with PBS to remove the detached cells and then cultured in serum-free medium in the presence of mitomyocin C (10 µg/ml) to prevent cell proliferation. The rate of wound healing was quantified as described in the literature Western blotting and protein co-immunoprecipitation. Cells or wounded tissues were sonicated on ice in RIPA buffer containing 1% NP-40, 0.5% deoxycholate and a protease/phosphatase inhibitor cocktail (Roche Diagnostics) and the resulting homogenates were centrifuged at 15,000 g for 15 min at 4° C. The Protein concentrations in the supernatants were determined by the BCA Protein Assay (Pierce). For immunoprecipitation, 500 µg protein was incubated with 20 µl Protein A-G (Santa Cruz Biotechnology, USA) and 5 µg antibody overnight at 4° C. under constant rotation. Nonspecific IgG was used as a negative control. Immunoprecipitates were washed 2× with RIPA buffer before the addition of 2× Laemmli buffer. Proteins derived from the lysates and immunoprecipitates were loaded onto an SDS-polyacrylamide gel and transferred to a polyvinylidenedifluoride membrane (Bio-Rad). The membranes were blocked and then incubated with the primary antibody diluted in 5% non-fat dry milk in TBST buffer (10 mM Tris-HCl, pH 7.5, 150 mM NaCl, 0.05% Tween 20) overnight at 4° C. After washing, the blots were incubated with the secondary antibody conjugated to HRP in TBST for 1 hr at room temperature. The proteins were visualized with the Super Signal West PicoChemiluminescent Substrate (Pierce) according to the manufacturer's protocol.

Real-time PCR for mRNA quantitation. Total RNA from cells or frozen wounded tissues was extracted using the Trizol reagent (Invitrogen), and the integrity of the RNA was verified using agarose gel electrophoresis. Approximately 1 µg of RNA was reversed transcribed (Superscript II Reverse Transcriptase Kit, Invitrogen) and amplified using the TaqMan Assay on Demand (Applied Biosystems) in a 25 µl reaction volume containing two unlabeled primers, a 6-carboxyfluorescien-labeled TaqMan MGB probe and the master mix. The amplified sequences were assessed using the ABI 7500 Prism Sequence Detection system machine. The results were expressed as mRNA levels normalized to 18S or GAPDH in each sample.

Total antioxidant capacity (TAC) and NADPH/NADP assays. The TAC in fibroblasts and wounded tissues were assessed by Trolox equivalent antioxidant capacity using a standard antioxidant assay kit (Cayman, USA). Briefly, samples were homogenized in phosphate buffer (pH 7.4) containing 0.9% NaCl and 0.1% glucose. The resulting homogenates were centrifuged at 10,000 g for 15 min at 4° C. and the resulting supernatant was collected and used in the assay according to the manufacturer's instruction. Similarly, quantification of NADPH and NADP in fibroblasts and wounded tissues were conducted on the basis of the differential sensitivities of these two forms of nucleotides to heat using the enzymatic recycling assay kit (Biovision, USA).

SiRNA/cDNA transfection. The expression of caveolin-1 in fibroblasts of type 2 diabetes was abolished by siRNA oligonucleotides. The sequences were designed and synthesized by Qiagen (USA). The day before transfection, cells were seeded at a density of 1.75×105 cells/well in a six-well plate in complete DMEM medium. The next day, cells were washed once with OptiMEM medium (Gibco, USA) and then overlaid with 800 µl of OptiMEM medium. Optimum silencing efficiency was obtained by adding 15 µl of 20 µM siRNA to 145 µl of 37° C. OptiMEM medium and this mixture was incubated at room temperature for 15 min. Thereafter, Oligofectamine (8 µl, Invitrogen, USA) was added to 32 µl of OptiMEM medium and after 5 min, the Oligofectamine mixture was added to the siRNA tube. Complexes were allowed to form for 15 min, and then they were added to the cells. After 4 hrs of incubation in the CO2 incubator, 500 µl of DMEM containing 30% FCS were added to the well. Following overnight incubation, the cells were washed with PBS, incubated in DMEM medium and used for the various assays related to the caveolin-1 knockdown. As for overexpression of Cav-1, pCMV6 (vector) and pCav-1 (plasmid that overexpresses rat Cav-1) were purchased from OriGene Technologies Inc. (USA) and Lipofectamine 2000 (Invitrogen, USA) was used for the transfection Efficiencies of the knockdown and overexpression of Cav-1 was verified by real-time PCR or Western blotting.

Wound model, drug treatment and macroscopic evaluation. All of the animal procedures were performed in accordance with the NIH Guidance for the Care and Use of Laboratory Animals. Female GotoKakizaki rats (GK) were used in the current study. Detailed information regarding this animal model for non-obese type 2 diabetes has been previously described. Weight and age-matched female Wistar rats (Kuwait University breeding colony) served as the corresponding controls. All of the animals were maintained under standard conditions with a 12 hour on/off light cycle, commercial diet, and water ad libitum. GK rats destined for wounding were initially matched with regard to body weight (e.g., 250 to 300 g) and plasma levels of glucose, free fatty acids and insulin. These indices are commonly used to reflect the severity of the diabetic state.

The animals were anesthetized by intraperitoneal injection of 90 mg ketamine+10 mg xylazine/kg body weight, and their back skin was shaved, depilated with Nair and cleaned with 70% alcohol. Six bilateral full-thickness excisional wounds (8 mm in diameter) equidistant from the midline were created on the dorso-rostral back skin. The wounds were separated by a minimum of 1 cm of uninjured skin.

The targeted depletion of caveolin-1 was achieved using the antisense vivo-morpholino oligomers (MOs) that were synthesized and designed by Gene Tools, LLC (Eugene, Oreg.). Antisense or 4-mismatch negative control MOs at 75 µM were applied to the wound in a vehicle of pluronic acid in phosphate buffered saline solution. The specificity of the cav-1 morphant phenotype was determined using rat caveolin-1 cRNA that lacked the antisense MO binding site. The efficiency of the knock out was confirmed using a western blotting-based technique. The wounds were photographed at various time intervals after injury (0-, 1-, 3-, 5-, 7-, 10- and 14-day; only the 10-day period is shown) using a Sony D-9 digital camera. The wound area was analyzed using Adobe Photoshop (version 7.0; Adobe Systems), and the percentage of wound closure was derived by the following formula: (1−[current wound size/initial wound size])×100. A maximum effect of the vivo-Morpholino caveolin-1 anti-sense-based therapy was observed macroscopically at day 10 during the course of wound healing and henceforth, it was used to study the various parameters related to cav-1 signaling, pro-oxidant and anti-oxidant capacity and the biochemical markers of cellular senescence. It is noteworthy that previous studies have indicated that the 7- to 10-day period is a critical time not only for healing but also for growth factor activity.

Statistical analysis. The data are expressed as the means±SEM. A one-way analysis of variance with Bonferroni post hoc validation or the Mann-Whitney test was used to compare the data derived from various experimental groups. A level of P≤0.05 was considered to be significant.

Example 1

Senescence-Like Features and a Reduction in the Maintenance of Cellular Redox Balance in DFs and OD-CFs Control (CFs, n=3), diabetic (DFs, n=4), and oxidatively stressed control fibroblasts (OS-CFs, i.e., fibroblasts that were exposed to hydrogen peroxide, 150 μM for three passages; n=4) were assessed for the presence of key biomarkers of cellular senescence. SA-β-gal activity was assessed by either staining cells with a chromogenic X-gal-based cocktail solution and visualizing the blue coloration of the cytoplasm by light microscopy or by incubating cellular protein extracts with MUG fluorogenic substrate and determining the rate of conversion to the fluorescent 4-MU product with a fluorometer. pH2AX contents were either visualized by immunofluorescence staining assay using Texas Red-tagged goat anti-rabbit IgG as the secondary antibody, or quantified by a DNA damage assay kit. Cells were seeded (N0) in DMEM supplemented with 10% FCS and were harvested at confluence (Nf). The cell population doubling was calculated as described below. The rate of DNA synthesis was measured by quantifying the rate of BrdU incorporation into DNA using a commercially available ELISA-based assay. The expression of p53 and p21 was monitored by Western blotting using the indicated antibodies. B-actin was used as an internal control. Maintenance of cellular redox balance expressed in terms of NADPH/NADP ratio and the mRNA levels of glucose-6-phosphate dehydrogenase and thioredoxinreductase or total antioxidant capacity was monitored using, respectively, spectrophotometric-, Taq-Man real-time PCR-based technique, or an ELISA-based technique. Most of the assays were performed in triplicate, and data was expressed as the means±SEM of at least three independent experiments. DFs and OD-CFs displayed senescence-like features and a reduction in the maintenance of cellular redox balance. The data obtained for DFs and OD-CFs was significantly different from corresponding control values at P≤0.05.

In particular, as noted earlier, the data revealed that DFs showed a marked enhancement in SA-β-gal expression (FIG. 4 is representative), increased DNA damage foci accompanied by histone H2AX phosphorylation (FIG. 5 is representative), and growth inhibition The latter process was illustrated in the current study by assessing two biological cell proliferation markers, including the rate of cell doubling per day and BrdU incorporation, a measure of the rate of DNA synthesis. Moreover, the expression of p53 and p21, key regulators of cellular senescence, were also upregulated in DFs when compared to their control counterparts. Interestingly, these phenotypic features of senescence in DFs were associated with an aberration in the systems that are involved in reductive biosynthesis (NADPH/NADP$^+$), maintenance of the cellular redox balance and ROS scavenging (e.g., mRNA levels of G6PD and thioredoxinreductase. Consistent with these data, we also confirmed in DFs a significant reduction in total antioxidant capacity in situ, quantified using a Trolox-based assay.

Example 2

DFs and OS-CFs Exhibited a Significant Increase in Caveolin-1 Expression and Attenuation in Growth Factor Actions Control (n=3), diabetic (n=4), and oxidatively stressed control fibroblasts (e.g., control fibroblasts exposed to hydrogen peroxide, 150 μM for three passages; n=4) were used to assess caveolin-1 expression and the actions of growth factors. Caveolin-1 protein expression and PDGF-induced phosphorylation of Akt (20 min) and ERK (10 min) in 24-hr serum starved fibroblasts were determined using a Western-blotting-based technique. A proliferation index encompassing BrdU incorporation into DNA and cell cycle progression was evaluated in response to various growth factors (e.g., IGF, 50 ng; PDGF, 1 nM; EGF, 100 ng) in 24-hr serum starved fibroblast. An in vitro wound-healing model conducted by scratching starved confluent cultured fibroblasts with a pipette tip was used to monitor the impact of PDGF on cell migration. Most of the assays were performed in triplicate, and the data are expressed as the means±SEM of at least three independent experiments. DFs and OS-CFs exhibited a significant increase in caveolin-1 expression and attenuation in growth factor actions compared to corresponding control values at P≤0.05. As noted earlier, the data obtained confirmed that the Cav-1 level was markedly increased in DFs compared to their control counterparts. In particular, diabetes-induced Cav-1 upregulation was found to be apparently associated with impaired PDGF ability to regulate the phosphorylation-dependent activation of Akt and ERK1/2. In serum-induced proliferating cells in CFs, the optical density at 450 nm (OD450) was more than 10-fold higher than that observed for starved cells. Similarly, PDGF, EGF and IGF also increased the proliferation rate by approximately 10-fold, 7.1-fold and 6.7-fold, respectively. This stimulatory action of the growth factors on cell proliferation was markedly suppressed in diabetic conditions as shown by Example 3.

Example 3

Effects of Caveolin-1 Overexpression and Deficiency on Cellular Senescence and Key Fibroblast Functions Essential for Wound Healing CFs were transfected with caveolin-1-pCMV(pCMV-Cav-1) or its vector control (pCMV-GRP), whereas DFs were rendered caveolin-1 deficient (Cav-1 siRNA) using siRNA-based technique. Transfection efficiency in both cases was confirmed using Taq-Man real-time PCR and Western blotting. After culturing for 48 hrs, cells were assessed in terms of senescence biomarkers, as in the case of SA-β-gal activity (fluorescence-based assay kit), pH2AX contents (fluorescence-based assay kit), and the protein expression of p53 (western blotting) and p21 (Western blotting) using fluorescence-based assay kits or Western blotting. Similarly, pCMV-Cav-1 and Cav-1 siRNA were also evaluated in the context of PDGF actions on p-Akt levels and key fibroblasts functions essential for wound healing, including BrdU incorporation into DNA (spectrophotometer-based assay kit) and cell migration (scratch with a pipette tip followed by light microscope-based measurement). Most of the assays were performed in triplicate, and the data was expressed as the means±SEM of at least three independent experiments As noted earlier, the tendency of the diabetic state to induce premature senescence, as reflected by the increase in SA-β-gal activity, was found to be reduced in cells harboring the Cav-1 siRNA (FIG. 6). The tendency of the diabetic state to induce premature senescence, as reflected by the increase in the levels of pH2AX, p53, and p21 was also found to be reduced in cells harboring the Cav-1 siRNA. Consistent with these findings, reducing Cav-1 level in DFs using the siRNA-based technique partially restored PDGF responses, as exemplified by the increased phosphorylation of p-Akt and the enhanced rates of cellular proliferation (e.g., DNA synthesis) (FIG. 7) and migration (FIG. 8). Overall, the data obtained by the present inventors supports the notion that cellular senescence (e.g., level/activity of SA-β-gal, pH2AX, p53, p21) and decreased rates of cell proliferation and migration in DFs may stem, at least in part, from Cav-1 overexpression. More intriguingly, a functional recovery of DFs, in terms of growth factor responsiveness, appears to be attainable by instituting a therapeutic strategy that reduces the Cav-1 level.

Example 4

PTRF-Mdm2-Dependent Signaling Contributes to Caveolin-1-Induced Cellular Senescence in OS-CFs and DFs PTRF/Cavin-1 and Mdm2 expression were measured in total cell lysates by Western blotting. A coimmunoprecipitation-based assay was used to assess the interaction of caveolin-1 with PTRF and Mdm2 or the binding of p53 to Mdm2. PTRF in DFs was knocked down using an siRNA-based technique, and 48 to 72 hrs afterward, the cells were used for the assessment of SA-β-gal activity/pH2AX contents, the expression of p53, and the effects of PDGF on cell proliferation/migration. Most of the assays were performed in triplicate, and the data are expressed as the means±SEM of at least three independent experiments. Data confirmed that PTRF-Mdm2-dependent signaling contributes to caveolin-1-induced cellular senescence in OS-CFs and DFs.

As noted earlier, protein expression of PTRF was markedly increased in DFs when compared to their corresponding control values. A co-immunoprecipitation-based assay was used to assess the interaction of caveolin-1 with PTRF and Mdm2, as well as the binding of p53 to Mdm2. Co-immunoprecipitation studies in DFs demonstrated a significant enhancement in the binding of PTRF to Cav-1, and also of Cav-1 to Mdm2. PTRF in DFs was knocked down using an siRNA-based technique, and 48 to 72 hours afterward, the cells were used for the assessment of SA-β-gal activity/pH2AX contents (FIG. 9), the expression of p53 (FIG. 10) and the effects of PDGF on cell proliferation/migration (FIG. 11). The siRNA sequences were designed and synthesized by Qiagen (USA), catalogue number S102655450. The binding affinity of p53 for Mdm2 was markedly suppressed as a function of diabetes. The current findings suggest a sequence of events in which a heightened state of oxidative stress in DFs upregulates PTRF/cavin-1 protein expression, which, in turn, promotes the membrane localization of Mdm2 and its interaction with the already overexpressed Cav-1. This increase in the sequestration of Mdm2 by Cav-1 in DFs activates the p53/p21-dependent pathway, with the concomitant induction of cellular senescence. Support for the aforementioned proposition is best exemplified by data obtained by the present inventors showing that PTRF downregulation in DFs via an siRNA-based strategy reduced not only the levels of SA-β-gal and pH2AX (FIG. 9) but also the activity of p53 (FIG. 10). Moreover, partial restoration of PDGF activity, viewed in the context of cell proliferation/migration and Akt phosphorylation, was also evident in the siRNA-PTRF-DFs (FIG. 11).

Example 5

In Vivo-Morpholino-Based Knockdown of Caveolin-1 Ameliorated Both Premature Senescence and Impaired Wound Healing in Type 2 Diabetes Full-thickness excisional wounds were induced in the control and GK (a non-obese genetic model of type 2 diabetes), and key parameters related to cellular senescence, caveolin-1 signaling and oxidative stress were measured 10 days post-injury. SA-f-gal activity and pH2AX contents were measured using fluorescence-based assay kits. A protein expression of caveolin-1, PTRF, p53 and p21 in a 10-day wound was determined by Western blotting. A co-immunoprecipitation/Western blotting-based technique was used to assess the binding of caveolin-1 to PTRF or the Mdm2 to caveolin-1 and p53. The pro-oxidant and antioxidant capacities in a 10-day wound were quantified using spectrophotometry, ELISA and TaqMan real-time PCR. The rate of healing was evaluated macroscopically, as described above. An in vivo anti-sense morpholino-based caveolin-1 administered with pluronic acid was used to negate the diabetes-induced elevation in caveolin-1 wound contents. Parameters related to cellular senescence (e.g., SA-β-gal activity and pH2AX contents), Caveolin-1 signaling (e.g., protein expression of B, caveolin-1; C, PTRF; D, p53; E, p21 and F, protein binding of Mdm2 to caveolin-1 and p53 or caveolin-1 to PTRF), Pro-oxidant and anti-oxidant capacities (NADPH oxidase activity and NOX-1 mRNA levels; H, G6PD, TR mRNA levels and NADPH/NADP ratio; I total antioxidant capacity), were assessed. Rate of wound healing was determined using a 10-day control, diabetic and in vivo-Morpholino-treated diabetic wounds. Most of the assays were performed in triplicate, and the data are expressed as the means±SEM of at least 8 animals/group. In vivo-morpholino-based knockdown of caveolin-1 ameliorated both premature senescence and impaired wound healing in type 2 diabetes.

As noted earlier, this novel wound-based knockdown strategy ameliorated the diabetes-related increase in wound contents of SA-β-gal/pH2AX (FIG. 12), Cav-1, PTRF, p53 and p21. Moreover, the enhanced binding of Cav-1 to Mdm2 and PTRF and the decreased affinity of Mdm2 for p53 in a 9-day diabetic wound was also restored almost to normal values in response to the in vivo-Morpholino treatment. The above beneficial effect of Cav-1 knockdown in diabetic wounds was not limited to the senescence and Cav-1 signaling pathway, but extended also to the heightened state of oxidative stress. In this connection, total antioxidant capacity, the ratio of NADPH/NADP, and the level of expression of G6PD and TR were increased in MO-D when compared to corresponding vehicle-treated diabetic wounds. These data regarding the antioxidant capacity are of interest, especially when viewed in the context of the findings showing that over-expression of Cav-1, like that of diabetes, suppressed the activity of Nrf2 and its associated phase 2 dependent anti-oxidant enzymes. The most intriguing and novel finding, however, lies in the fact that delayed healing in diabetic wounds can be ameliorated by a genetic knockdown of Cav-1 (FIG. 13). FIGS. 12-13, respectively, summarize data obtained regarding diabetes-related increase in wound contents of SA-β-gal/pH2AX and rate of wound healing assessed using a 10-day control wound (C), diabetic wound (D) and in vivo-Morpholino-treated diabetic wound (MO-D).

It is to be understood that the present invention is not limited to the embodiments described above, but encompasses any and all embodiments within the scope of the following claims.

We claim:

1. A method of treating delayed healing of a wound associated with premature cellular senescence induced by diabetes, comprising the step of administering to the wound a composition comprising an anti-senescence compound and a pharmaceutically acceptable carrier, wherein the anti-senescence compound is a Caveolin-1 (Cav-1) inhibitory compound.

2. The method of treating delayed healing of a wound associated with diabetes as recited in claim 1, wherein the anti-senescence compound comprises an antisense oligonucleotide for inhibiting expression of Cav-1.

3. The method of treating delayed healing of a wound associated with diabetes as recited in claim 2, wherein the antisense oligonucleotide is a Morpholino antisense oligonucleotide.

4. The method of treating delayed healing of a wound associated with diabetes as recited in claim 1, wherein the anti-senescence compound comprises an siRNA for inhibiting expression of Cav-1.

5. The method of treating delayed healing of a wound associated with diabetes as recited in claim 1, wherein the pharmaceutically acceptable carrier comprises pluronic acid.

6. The method of treating delayed healing of a wound associated with diabetes as recited in claim 1, wherein the anti-senescence compound is present in a concentration range of 30 μM to 100 μM.

7. The method of treating delayed healing of a wound associated with diabetes as recited in claim 1, wherein the wound is a diabetic ulcer.

8. The method of treating delayed healing of a wound associated with diabetes as recited in claim 1, wherein the wound is a venous ulcer.

* * * * *